United States Patent [19]
Byrne

[11] Patent Number: 5,029,756
[45] Date of Patent: Jul. 9, 1991

[54] DISPENSING DEVICE

[75] Inventor: John R. Byrne, Watertown, Wis.

[73] Assignee: Vaportek, Inc., Sussex, Wis.

[21] Appl. No.: 367,688

[22] Filed: Jun. 19, 1989

[51] Int. Cl.$^5$ .............................................. A61L 9/04
[52] U.S. Cl. ..................................................... 239/59
[58] Field of Search ....................... 220/306, 253, 360; 239/58, 59; 206/17; 222/545, 553

[56] References Cited

U.S. PATENT DOCUMENTS

| | | | |
|---|---|---|---|
| 153,809 | 8/1874 | Conroy | 220/253 X |
| 1,344,601 | 6/1920 | Walgren | 220/306 X |
| 2,103,609 | 12/1937 | Bradburn | 239/59 X |
| 2,239,145 | 3/1966 | Russo | 239/58 X |
| 2,556,608 | 6/1951 | Will | 239/58 X |
| 2,738,225 | 3/1956 | Meek | 239/59 X |
| 2,765,194 | 10/1956 | Will | 239/59 |
| 3,785,556 | 1/1974 | Watkins | 239/ |
| 3,790,081 | 2/1974 | Thornton et al. | 239/59 X |
| 4,096,995 | 6/1978 | Bryson | 239/ |
| 4,377,399 | 3/1983 | Bryson | 239/59 X |
| 4,544,063 | 10/1985 | Neward | 220/253 X |

Primary Examiner—Andres Kashnikow
Assistant Examiner—Kevin Weldon
Attorney, Agent, or Firm—Michael, Best & Friedrich

[57] ABSTRACT

Disclosed herein is a dispensing device comprising a housing assembly including an outer housing including an end wall having therein an opening, a side wall extending from the end wall and terminating at an open end spaced from the end wall, a second end wall having therein an opening, and interengaging structure on the outer housing and on the second end wall for releaseably connecting the outer housing to the second end wall, an inner housing including an end wall having therein an opening, a side wall extending from the end wall of the inner housing and terminating in an open end spaced from the end wall of the inner housing and forming an opening, and a pin and socket arrangement on the outer housing and on the second end wall for supporting the inner housing within the outer housing assembly and for rotation between a first position wherein the openings in the inner housing register with the openings in the outer housing assembly, and a second position located in spaced relation to the first position and wherein the openings in the inner housing are out of registry with the openings in the outer housing assembly.

24 Claims, 2 Drawing Sheets

U.S. Patent July 9, 1991 Sheet 1 of 2 5,029,756
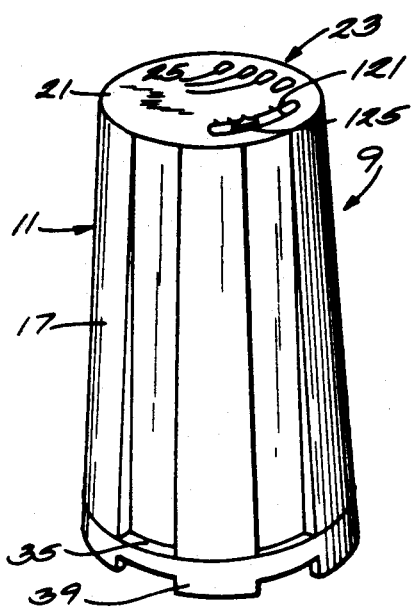
Fig. 1
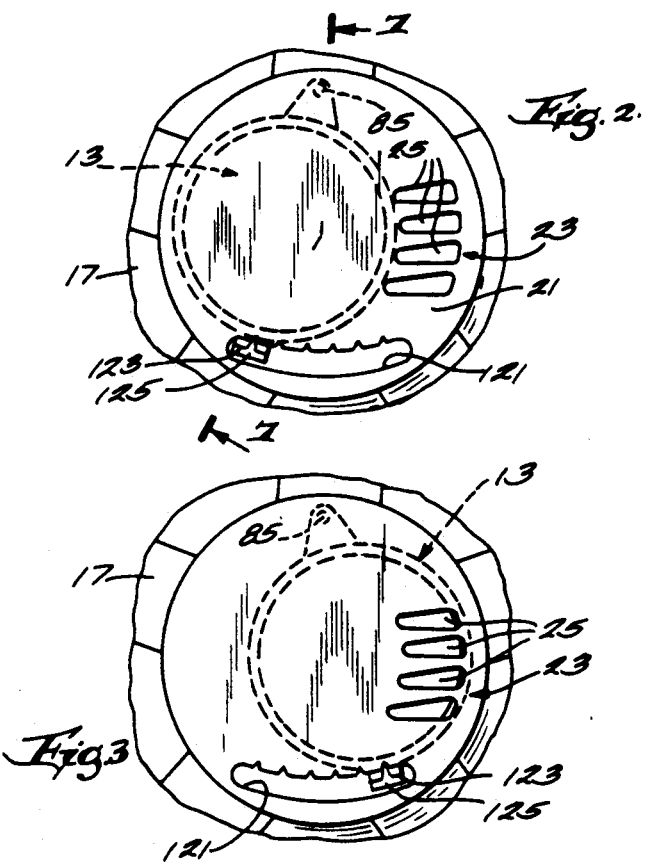
Fig. 2
Fig. 3
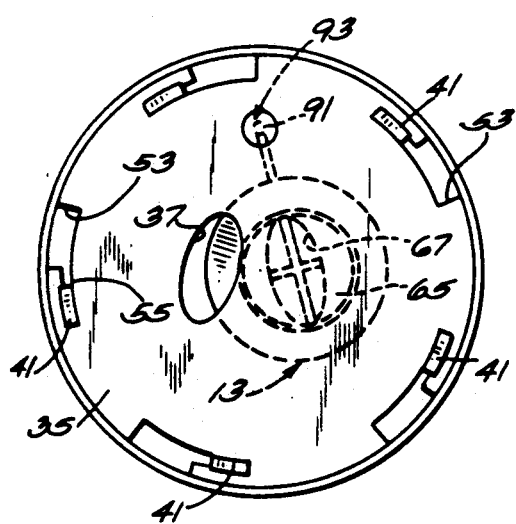
Fig. 4
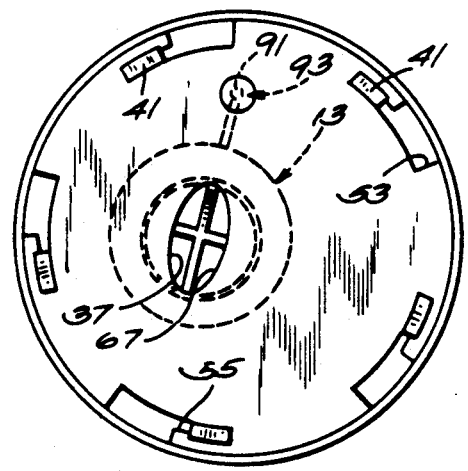
Fig. 5

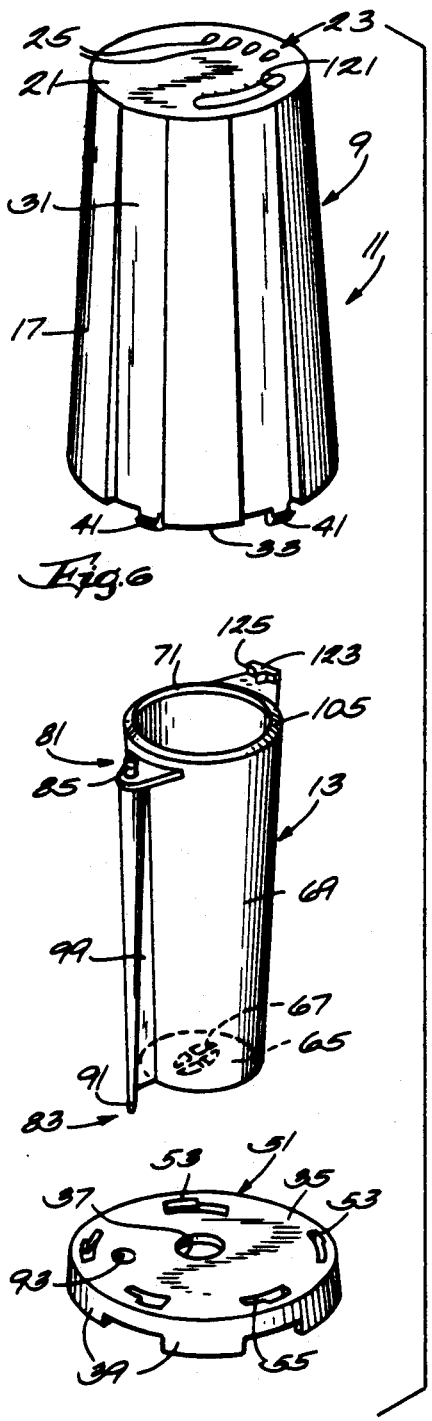
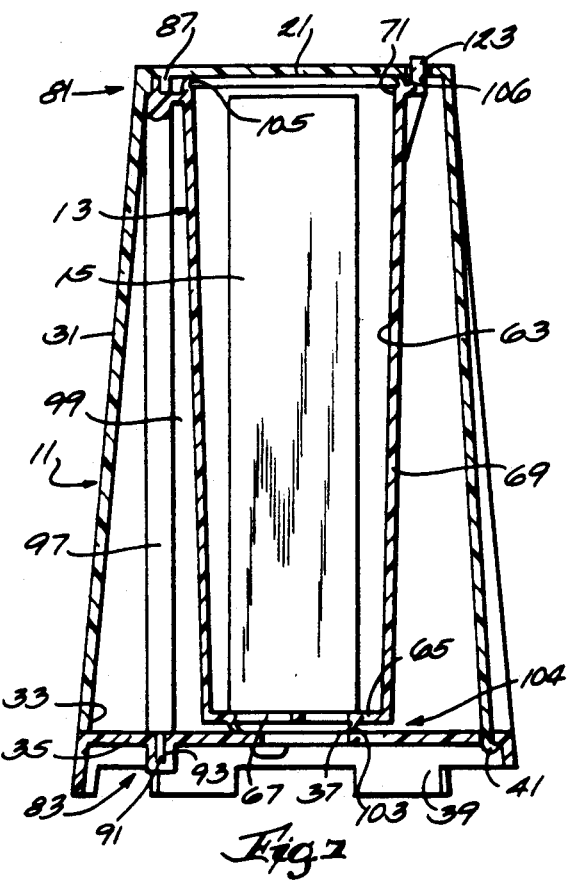
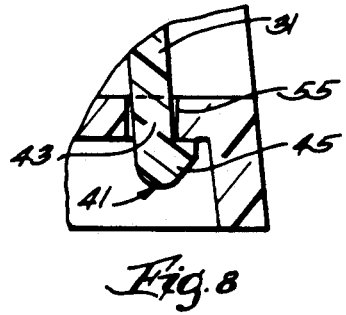
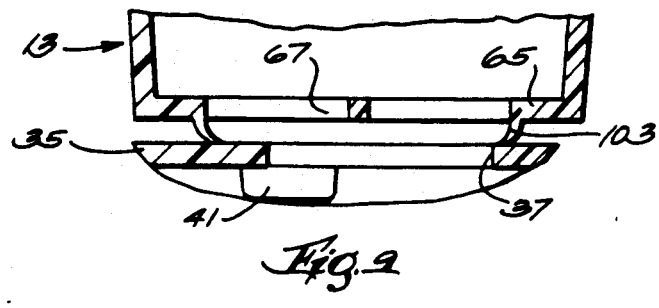

DISPENSING DEVICE

BACKGROUND OF THE INVENTION

1. Field of Invention

The invention relates generally to dispensers which can be manually manipulated to afford selective displacement of an active ingredient contained within the dispenser. The invention also relates to dispensers for active ingredients which are releaseable through a membrane to the atmosphere.

2. Reference to Prior Art

Attention is directed to U.S. Pat. No. 4,096,994, issued June 27, 1978 and directed to a manual deorderizer dispenser and to U.S. Pat. No. 3,785,556 which discloses an envelope or package including a membrane through which an active ingredient is released.

SUMMARY OF THE INVENTION

The invention provides a dispensing device comprising a housing assembly including an end wall having therein an opening, a side wall extending from the end wall and terminating at an open end spaced from the end wall, a second end wall having therein an opening, and means on the outer housing and on the second end wall for releaseably connecting the outer housing to said second end wall, an inner housing including an end wall having therein an opening, a side wall extending from the end wall of the inner housing and terminating in an open end spaced from the end wall of the inner housing and forming an opening, and means on the outer housing and on the second end wall for supporting the inner housing within the outer housing assembly and for movement between a first position wherein the openings in the inner housing register with the openings in the outer housing assembly, and a second position located in spaced relation to the first position and wherein the openings in the inner housing are out of registry with the openings in the outer housing assembly.

The invention also provides a dispensing device comprising a housing assembly including an outer housing including an end wall having therein an opening, a side wall extending from the end wall and terminating at an open end spaced from the end wall, a second end wall having therein a second opening, and means on the outer housing and on the second end wall for releaseably connecting the outer housing to the second end wall, an inner housing including an end wall having therein an opening, a side wall extending from the end wall of the inner housing and terminating in an open end spaced from the end wall of the inner housing, means on the outer housing and on the second end wall for supporting the inner housing within the outer housing assembly with the open end of the inner housing located adjacent the end wall of the outer housing and with the end wall of the inner housing located adjacent the second end wall and for rotation between a first position wherein the opening in the end wall of the inner housing registers with the opening in the second end wall and wherein the open end of the inner housing registers with the opening in the end wall of the outer housing, and a second position located in spaced relation to the first position and wherein the opening in the end wall of the inner housing is out of registry with the opening in the second end wall and wherein the open end of the inner housing is out of registry with the opening in the end wall of the outer housing, which means for rotatably supporting the inner housing within the outer housing comprises, adjacent the end wall of the outer housing, a pivot pin extending from the inner housing and a socket located in the end wall of the outer housing and receiving the pivot pin, and, adjacent the second end wall, a pivot pin extending from the inner housing and a socket located in the second end wall and receiving the last mentioned pivot pin, and sealing means on one of the end wall of the outer housing and the end of the side wall of the inner housing for sealingly engaging the other of the end wall of the outer housing and the end of the side wall of the inner housing to substantially prevent gaseous flow between the inner housing and the outer housing while affording relative movement therebetween, and sealing means on one of the second end wall and the end wall of the inner housing for sealingly engaging the other of the second end wall and the end wall of the inner housing to substantially prevent gaseous flow between the inner housing and the outer housing while affording relative movement therebetween.

Other features and advantages of the invention will become apparent to those skilled in the art upon review of the following detailed description, claims, and drawings.

THE DRAWINGS

FIG. 1 is a perspective view of a dispenser incorporating various features of the invention.

FIG. 2 is a fragmentary view of the top of the dispenser shown in FIG. 1 with the components thereof in a non-dispensing position.

FIG. 3 is a fragmentary view of the top of the dispenser shown in FIG. 1 with the components thereof in a dispensing position.

FIG. 4 is a fragmentary view of the bottom of the dispenser shown in FIG. 1 with the components thereof in a non-dispensing position.

FIG. 5 is a fragmentary view of the bottom of the dispenser shown in FIG. 1 with the components thereof in a dispensing position.

FIG. 6 is an exploded perspective view of the dispenser shown in FIG. 1.

FIG. 7 is a vertical sectional view taken generally along line 7—7 of FIG. 2.

FIG. 8 is an enlarged view of a portion of FIG. 7.

FIG. 9 is an enlarged view of another portion of FIG. 7.

Before one embodiment of the invention is explained in detail, it is to be understood that the invention is not limited in its application to the details of the construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF A PREFERRED EMBODIMENT

Shown in the drawings is a dispenser 9 which incorporates various of the features of the invention and which includes an outer housing assembly 11 having therein an inner housing 13 adapted to contain (see FIG. 7) a package or envelope 15 containing an active ingredient or agent and which is movable selectively between a position affording dispensing from the inner housing 13 of the active ingredient and a position preventing such dispensing. The package can take the form of the package disclosed in U.S. Pat. No. 3,785,556.

More particularly, the outer housing assembly 11 includes an outer housing 17 which is of elongated and generally cylindrical construction. In the specifically disclosed construction, the outer housing 17 is of frustroconical shape. Still more specifically, the outer housing 17 includes an end wall 21 which is generally of disc shape, which is closed or solid except for a dispensing opening 23, and as will otherwise be disclosed hereinafter. The dispensing opening 23 can take various configurations and, in the disclosed construction, comprises a series of narrow elongated and closely spaced slots 25.

The outer housing 17 also includes a side wall 31 which extends from the end wall 21, which is closed or solid throughout, and which, in spaced relation to the end wall 21, defines an open end 33.

The outer housing assembly 11 also includes a second end wall 35 which is generally of disc shape and which is solid or closed except for a dispensing opening 37 therein, and except as will hereinafter be disclosed.

The second end wall 35 is also provided with a plurality of legs or feet 39 which extend in spaced relation to each other and which facilitate support of the dispenser 9 on a supporting surface with the second end wall 35 located above the supporting surface and in communication with the environment through the spaces between the legs or feet 39.

The outer housing assembly 11 also includes means on the outer housing 17 and on the second end wall 35 for removable connection therebetween. While various arrangements can be employed, in the disclosed construction, such means comprises, on one of the outer housing 17 and the second end wall 35, a series of arcuately spaced tangs or tabs 41 which respectively include inner portions 43 of generally smaller dimension and outer hook-shaped end portions 45 of generally larger dimensions, and, on the other of the outer housing 17 and the second end wall 35, a like series of arcuately spaced and extending slots 51 respectively including relatively enlarged end portions 53 permitting passage therethrough of the hooked shaped end portions 45 of the tabs 41, and opposite relatively narrow end portions 55 dimensioned to permit entry thereinto of the inner portions 43 of the tabs 41, but to prevent passage therethrough of the enlarged hook-shaped end portions 45 of the tabs 41, thereby selectively affording assembly and disassembly of the second end wall 35 with the outer housing 17 and preventing unwanted disassembly of the second end wall 35 from the outer housing 17.

The inner housing 13 is also generally of cylindrical shape and, in the specifically disclosed construction, is of frustroconical shape and defines an interior space or chamber 63. The inner housing 13 includes an end wall 65 which is closed or solid except for a dispensing opening 67. The inner housing 13 also includes a side wall 69 which extends from the end wall 65, which is closed or solid and which defines, in spaced relation to the end wall 65, an open end 71 providing an opening into the chamber 63.

The dispenser 11 also includes means on the inner and outer housings 11 and 17, respectively, for supporting the inner housing 13 within the outer housing assembly 11 for movement between a first or dispensing position wherein the dispensing opening 23 in the end wall 21 of the outer housing 17 is in registry with the open end 71 of the inner housing 13, and wherein the dispensing opening 37 in the second end wall 35 and the dispensing opening 67 in the end wall 65 of the inner housing 13 are in registry, and a spaced second or non-dispensing position wherein the openings 37 and 67, respectively, located in the second end wall 35 and in the end wall 65 of the inner housing 13, are out of registry and wherein the open end 71 of the inner housing 13 is out of registry with the dispensing opening 23 in the end wall 21 of the outer housing 17. While various arrangements can be employed for such mounting, in the disclosed construction, such mounting is provided by first pin and socket means 81 adjacent the end wall 21 of the outer housing 17 and by second pin and socket means 83 provided adjacent the second end wall 35. Various pin and socket means can be employed, however, in the disclosed construction, the first pin and socket means 81 comprises a pivot pin 85 extending from one of the inner and outer housings 11 and 17, respectively, and a socket 87 which is located on the other of the inner and outer housings 11 and 17, respectively, and which receives the pivot pin 85. Still more specifically, in the disclosed construction, the inner housing 13 is provided with the pivot pin 85 and the end wall 21 of the outer housing 17 is provided with the socket 87 which is located adjacent to the side wall 31.

The second pin and socket means 83 can also take various forms and, in the disclosed construction, one of the inner housing 11 and the second end wall 35 includes a pivot pin 91 and the other of the inner housing 13 and the second end wall includes a socket 93 which receives the pivot pin 91. Still more sPecifically, in the disclosed construction, the Pivot Pin 91 extends from the inner housing 13 and is received in the socket 93 formed in the second end wall 35.

In the disclosed construction, the pivot pins 85 and 91 comprise end portions of a unitary shaft 97 which extends generally at a slight angle to the side wall 69 of the inner housing 13, which is integrally connected to the inner housing 13 by a web 99, which, when the second end wall 35 is assembled to the outer housing 17, extends in right angle relation to the end wall 21 of the outer housing 17 and to the second end wall 35, and which serves to reinforce the rotatable mounting of the inner housing 13 within the outer housing assembly 11.

Means are also provided for sealingly engaging the end wall 65 of the inner housing 13 with the second end wall 35 and for sealingly engaging the open end 71 of the inner housing 13 with the end wall 21 of the outer housing 17 when the second end wall 35 is assembled to the outer housing 17 so as to thereby prevent gaseous flow to or from the inner chamber 63 of the inner housing when the inner housing 13 is in the non-dispensing position. While various other arrangements can be employed, in the disclosed construction, such means is provided, adjacent the end wall 65 of the inner housing 13, by a flexible lip 103 which extends from the end wall 65 and around the dispensing opening 67 and which wipes or sealingly engages the second end wall 35 to provide a seal 104 which permits relative movement between the inner and outer housings 13 and 17, respectively.

At the other end of the dispenser 9, such means is provided by a flexible lip 105 which extends from the side wall 69 of the inner housing 13 and which, when the second end wall 35 is assembled to the outer housing 17, engages the adjacent surface of the end wall 21 of the outer housing 17 to provide a seal 106 which permits relative movement between the side wall 69 of the inner housing and the end wall 21 of the outer housing 17.

The seals 104 and 106 are effected in response to assembly of the second end wall 35 on the outer housing 17, which assembly places the flexible lips 103 and 105 of the inner housing 13 under axial compression or deflection against the end wall 21 of the outer housing 17 and the second end wall 35.

The dispenser 9 also includes means on the inner housing 13 and on the outer housing assembly 11 and extending, in part, exteriorly of the outer housing assembly 11 for rotating the inner housing 13 relative to the outer housing assembly 11. While various other arrangements can be employed, in the disclosed construction, such means comprises an aperture 121 in the outer housing assembly 11 and a control member 123 extending from the inner housing 13 and through the aperture 121 and including an outer end 125 manipulatable by a user. Still more specifically, in the disclosed construction, the aperture 121 is arcuate and is located in the end wall 21 of the outer housing 17 and the control member 123 extends from the open end 71 of the inner housing 13 and through the aperture 121 in the end wall 21 of the outer housing 17. Thus, the dispenser 9 can be grasped by a user and the outer end portion 125 manipulated to rotate the inner housing 13 within the outer housing assembly 11 between the dispensing and non-dispensing positions.

Located within the chamber 63 of the inner housing 13 is the package or envelope 15 which includes the active agent or ingredient to be dispensed. The package or envelope 15 desirably includes a membrane (not shown) through which the active ingredient or agent is passable. However, when the inner housing 13 is in the non-dispensing position, there is no air flow through the inner housing 13 and, accordingly, the rate of passage of the active agent through the membrane is substantially reduced or eliminated.

In use, when it is desired to dispense the active ingredient or agent to the surroundings, the dispenser 9 is gripped by the user, and the control member 123 is manipulated to locate the inner housing 13 in the dispensing position. The dispenser is then placed with the legs or feet 39 engaging the support surface. As a consequence, air can travel through the inner housing 13 between the openings at the ends thereof to carry the active ingredient from the inner housing 13. When it is no longer desired to dispense the active ingredient, the control member 123 can be gripped to rotate the inner housing 13 to the non-dispensing position and thereby prevent air flow through the inner housing 13. When the inner housing 13 is sealed from the environment, the air flow will stop and dispensing of the active ingredient from the dispenser 9 will be substantially prevented. In addition, the passage of the active ingredient from the envelope or package 15 to the inner housing 13 will be discouraged or substantially prevented.

When the active ingredient is substantially emptied from the envelope or package 15, the dispenser 9 can be opened by disassembling the second end wall 35 from the outer housing 17 and by removal of the inner housing 13 from the outer housing 17 so as to facilitate replacement of the package 15 in the inner housing 13. Thereafter, the inner housing 13 can be located in the outer housing 17 so that the pivot pin 85 extends in the socket 87 and so that the control member 123 extends through the aperture 121 in the end wall 21 of the outer housing 17. Thereafter the second end wall 35 can be located so as to insert the pivot pin 91 into the socket 93 and to insert the tabs 41 through the enlarged portions 53 of the slots 51. Rotation of the second end wall 35 relative to the outer housing 17 to locate the tabs 41 in the narrow end portions 55 of the slots 51 aligns the sockets 87 and 93 and engages the second end wall 35 with the outer housing 17 as well as the end wall 65 of the inner housing 13 with the second end wall 35 so that the seals 104 and 106, at the top and bottom of the inner wall 13, are established.

While other constructions could be employed, the inner housing 13, the outer housing 17, and the second end wall 35 are preferably all fabricated of plastic by die casting.

It is noted that the dispensing opening 37 in the second end wall 35, the dispensing opening 67 in the end wall 65 of the inner housing 13, and the dispensing opening 23 in the end wall 21 of the outer housing 17, are all dimensioned, shaped, and located so as to facilitate dispensing of the agent when the inner housing 13 is in the disPensing position and to prevent dispensing when the inner housing 13 is in the non-dispensing position.

Various of the features of the invention are set forth in the following claims.

I claim:

1. A dispensing device comprising a housing assembly including an outer housing including an end wall having therein an opening, and a side wall extending from said end wall and terminating at an open end spaced from said end wall, a second end wall having therein an opening, and means on said outer housing and on said second end wall for releaseably connecting said outer housing to said second end wall, an inner housing including an end wall having therein an opening, and a side wall extending from said end wall of said inner housing and terminating in an open end spaced from said end wall of said inner housing and forming an opening, and means for supporting said inner housing within said outer housing assembly and for movement between a first position wherein said openings in said inner housing register with said openings in said outer housing assembly, and a second position located in spaced relation to said first position and wherein said openings in said inner housing are out of registry with said openings in said outer housing assembly.

2. A dispensing device in accordance with claim 1 and further including sealing means extending integrally from one of said end wall of said outer housing and said end of said inner housing side wall for sealingly engaging the other of said end wall of said outer housing and said end of said side wall of said inner housing to substantially prevent gaseous flow between said inner housing and said outer housing while affording relative movement therebetween, and sealing means extending integrally from one of said second end wall and said end wall of said inner housing for sealingly engaging the other of said second end wall and said end wall of said inner housing to substantially prevent gaseous flow between said inner housing and said outer housing while affording relative movement therebetween.

3. A dispensing device in accordance with claim 2 wherein releaseable connection of said second end wall to said outer housing locates said sealing means in sealing engagement.

4. A dispensing device in accordance with claim 1 and further including means on said inner housing and on said outer housing assembly and extending, in part, exteriorly of said outer housing assembly for rotating said inner housing assembly relative to said outer housing.

5. A dispensing device in accordance with claim 4 wherein said means for rotating said inner housing relative to said outer housing assembly comprises an aperture in said outer housing assembly and a control member extending from said inner housing and through said aperture and including an outer end manipulateable by a user.

6. A dispensing device in accordance with claim 5 wherein said aperture is located in said end wall of said outer housing and said control member extends from said side wall of said inner housing adjacent said open end.

7. A dispenser in accordance with claim 1 wherein said means for rotatably supporting said inner housing within said outer housing comprises, adjacent said end wall of said outer housing, a pivot pin extending from one of said inner housing and said outer housing assembly and a socket located in the other of said inner housing and said outer housing assembly and receiving said pivot pin, and, adjacent said second end wall, a pivot pin extending from one of said inner housing and said outer housing assembly and a socket located in the other of said inner housing and said outer housing assembly and receiving said last mentioned pivot pin.

8. A dispenser in accordance with claim 7 wherein said pivot pin adjacent said end wall of said outer housing extends from said inner housing, wherein said socket adjacent said end wall of said outer housings is located in said end wall of said outer housing, wherein said pivot pin adjacent said second end wall extends from said inner housing, and wherein said socket adjacent said second end wall is located in said second end wall.

9. A dispenser in accordance with claim 8 wherein said pivot pins extending from said inner housing are coaxially aligned.

10. A dispensing device in accordance with claim 9 wherein said inner housing includes a shaft extending integrally between said pivot pins, and a web connecting said shaft to said side wall of said inner housing.

11. A dispenser in accordance with claim 1 wherein said means for releaseably connecting said outer housing and said second end wall includes a plurality of tabs extending outwardly from said end wall of said outer housing and respectively including inner portions and enlarged hooked shaped outer end portions, and wherein said second end wall includes a like plurality of arcuate slots respectively including enlarged end portions respectively accommodating passage therethrough of said hooked shaped end portions, and narrow end portions respectively accommodating arcuate passage of said inner portions of said tabs and preventing passage therethrough of said hooked shaped end portions of said tabs, thereby permitting assembly of said second end wall on said outer housing by passage of said tabs through said enlarged end portions of said slots and by subsequent rotation of said second end wall relative to said outer housing to a locked position wherein said inner portions are located in said narrow end portions of said slots and said hooked shaped end portions prevent disassembly of said second end wall from said outer housing.

12. A dispenser in accordance with claim 1 wherein said second end wall includes a plurality of legs extending therefrom and in spaced relation to one another for supporting said housing assembly in upright condition.

13. A dispensing device in accordance with claim 1 and further including, in said inner housing, a package of an active ingredient to be dispensed.

14. A dispensing device as set forth in claim 1 wherein said inner housing has a central axis and is supported for rotation about an axis spaced from and generally parallel to said central axis.

15. A dispensing device in accordance with claim 6 wherein said end wall defines the top of said outer housing.

16. A dispensing device comprising a housing assembly including an outer housing including an end wall having therein an opening, and a side wall extending from said end wall and terminating at an open end spaced from said end wall, a second end wall having therein a second opening, and means on said outer housing and on said second end wall for releaseably connecting said outer housing to said second end wall, an inner housing including an end wall having therein an opening, and a side wall extending from said end wall of said inner housing and terminating in an open end spaced from said end wall of said inner housing, means for supporting said inner housing within said outer housing assembly with said open end of said inner housing located adjacent said end wall of said outer housing and with said end wall of said inner housing located adjacent said second end wall and for rotation between a first position wherein said opening in said end wall of said inner housing registers with said opening in said second end wall and wherein said open end of said inner housing registers with said opening in said end wall of said outer housing, and a second position located in spaced relation to said first position and wherein said opening in said end wall of said inner housing is out of registry with said opening in said second end wall and wherein said open end of said inner housing is out of registry with said opening in said end wall cf said outer housing, said means for rotatably supporting said inner housing within said outer housing comprising, adjacent said end wall of said outer housing, a pivot pin extending from said inner housing and a socket located in the said end wall of said outer housing and receiving said pivot pin, and, adjacent said second end wall, a pivot pin extending from said inner housing and a socket located in said second end wall and receiving said last mentioned pivot pin, and sealing means on one of said end wall of said outer housing and said end of said side wall of said inner housing for sealingly engaging the other of said end wall of said outer housing and said end of said side wall of said inner housing to substantially prevent gaseous flow between said inner housing and said outer housing while affording relative movement therebetween, and sealing means on one of said second end wall and said end wall of said inner housing for sealingly engaging the other of said second end wall and said end wall of said inner housing to substantially prevent gaseous flow between said inner housing and said outer housing while affording relative movement therebetween.

17. A dispensing device in accordance with claim 16 wherein releaseable connection of said second end wall to said outer housing locates said sealing means in sealing engagement.

18. A dispensing device in accordance with claim 16 and further including means on said inner housing and on said outer housing assembly and extending, in part, exteriorly of said outer housing assembly for rotating said inner housing assembly relative to said outer housing.

19. A dispensing device in accordance with claim 18 wherein said means for rotating said inner housing relative to said outer housing assembly comprises an aperture in said end wall of said outer housing and a control member extending from said side wall of said inner housing adjacent said open end and through said aperture and including an outer end manipulateable by a user.

20. A dispensing device in accordance with claim 16 wherein said inner housing includes a shaft extending integrally between said pivot pins, and a web connecting said shaft to said side wall of said inner housing.

21. A dispenser in accordance with claim 16 wherein said means for releaseably connecting said outer housing and said second end wall includes a plurality of tabs extending outwardly from said end wall of said outer housing and respectively including inner portions and enlarged hooked shaped outer end portions, and wherein said second end wall includes a like plurality of arcuate slots respectively including enlarged end portions respectively accommodating passage therethrough of said hooked shaped end portions, and narrow end portions respectively accommodating arcuate passage of said inner portions of said tabs and preventing passage therethrough of said hooked shaped end portions of said tabs, thereby permitting assembly of said second end wall on said outer housing by passage of said tabs through said enlarged end portions of said slots and by subsequent rotation of said second end wall relative to said outer housing to a locked position wherein said inner portions are located in said narrow end portions of said slots and said hooked shaped end portions prevent disassembly of said second end wall from said outer housing.

22. A dispensing device in accordance with claim 16 and further including, in said inner housing, a package of an active ingredient to be dispensed.

23. A dispensing device comprising an outer housing including a first end having therein a first opening, a second end having therein a second opening, and a side wall extending between said first and second ends, an inner housing having a central axis and including a first end having therein a first opening, a second end having therein a second opening, and a side wall extending between said first and second ends of said inner housing, and means supporting said inner housing within said outer housing for pivotal movement relative thereto about an axis substantially spaced from and generally parallel to said central axis and for movement between a first position wherein said first opening in said inner housing registers with said first opening in said outer housing and said second opening in said inner housing registers with said second opening in said outer housing, and a second position located in spaced relation to said first position and wherein said first opening in said inner housing is out of registry with said first opening in said outer housing and said second opening in said inner housing is out of registry with said second opening in said outer hosing.

24. A dispensing device in accordance with claim 23 wherein said side wall of said inner housing is generally cylindrical, and wherein said pivot axis is spaced radially outwardly of said side wall of said inner housing.

* * * * *